Figure 1:
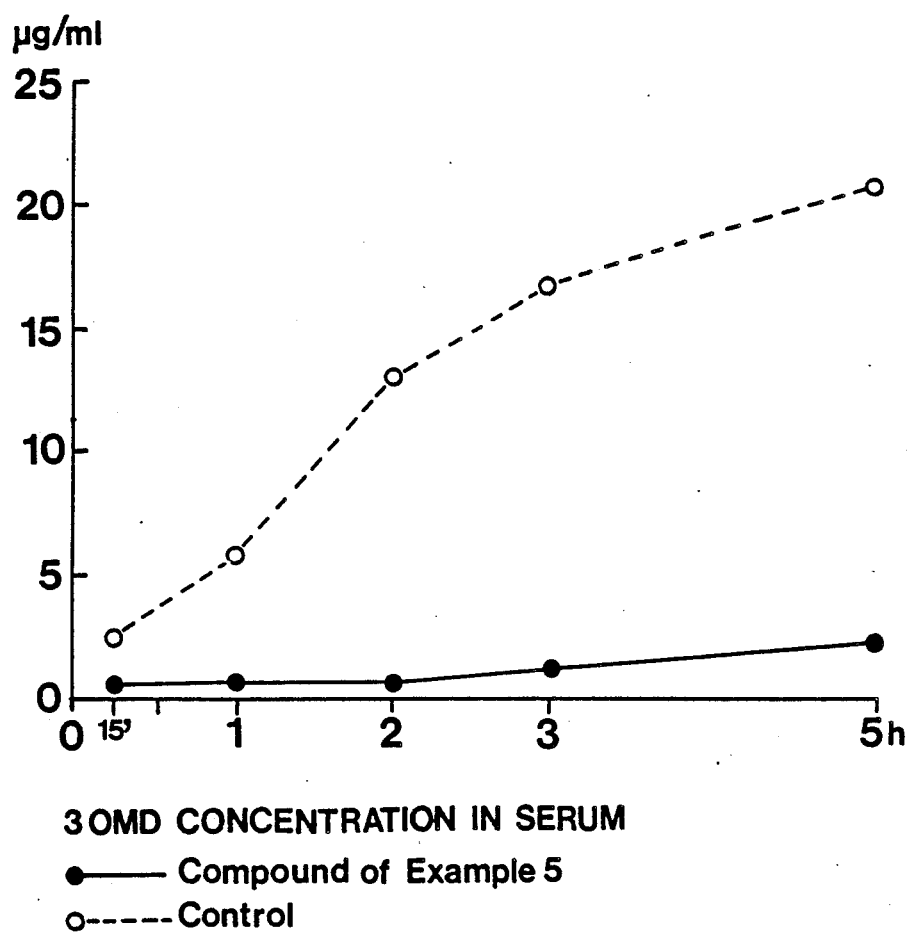

United States Patent [19]

Bäckström et al.

[11] Patent Number: 4,963,590
[45] Date of Patent: Oct. 16, 1990

[54] PHARMACOLOGICALLY ACTIVE COMPOUNDS, METHODS FOR THE PREPARATION THEREOF AND COMPOSITIONS CONTAINING THE SAME

[75] Inventors: Reijo J. Bäckström, Helsinki; Kalevi E. Heinola, Jävenpää ; Erkki J. Honkanen, Vantaa; Seppo K. Kaakkola, Helsinki; Pekka J. Kairisalo, Helsinki; Inge-Britt Y. Linden, Helsinki; Pekka T. Männistö, Helsinki; Erkki A. O. Nissinen, Espoo; Pentti Pohto, Helsinki; Aino K. Pippuri; Jarmo J. Pystynen, both of Espoo, all of Finland

[73] Assignee: Orion-yhtymä Oy, Finland

[21] Appl. No.: 126,911

[22] Filed: Nov. 27, 1987

[30] Foreign Application Priority Data

Nov. 28, 1986 [FI] Finland .................................. 864875

[51] Int. Cl.$^5$ ............................................ A61K 31/12
[52] U.S. Cl. ................................................... 514/678
[58] Field of Search ......................................... 514/678

[56] References Cited

FOREIGN PATENT DOCUMENTS

| | | |
|---|---|---|
| 0081321 | 6/1983 | European Pat. Off. . |
| 0125919 | 5/1984 | European Pat. Off. . |
| 0149952 | 12/1984 | European Pat. Off. . |
| 0237929 | 3/1987 | European Pat. Off. . |
| 0149407 | 4/1987 | European Pat. Off. . |
| 902586 | 1/1960 | United Kingdom . |
| 1188364 | 4/1970 | United Kingdom . |
| 1276966 | 6/1977 | United Kingdom . |
| 2008103A | 5/1979 | United Kingdom . |

OTHER PUBLICATIONS

Chemical Abstracts, vol. 79, 105449n.
Chemical Abstracts, vol. 104, 109112e.
Chemical Abstracts, vol. 95, 42542v.
Chemical Abstracts, vol. 92, 146461x.
Chemical Abstracts, vol. 79, 27554b.
Merck Index—Ninth Edition.

*Primary Examiner*—Stanley J. Friedman
*Attorney, Agent, or Firm*—Burns, Doane, Swecker & Mathis

[57] ABSTRACT

Pharmacologically active catechol derivatives of formula I

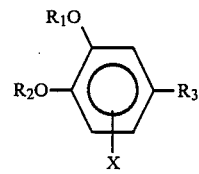

wherein $R_1$ and $R_2$ independently comprise hydrogen, alkyl, acyl, optionally substituted aroyl, lower alkylsulfonyl or alkylcabamoyl or taken together form a lower alkylidene or cycloalkylidene, X comprises an electronegative substituent such as halogen, nitro, cyano, lower alkylsulfonyl, sulfonamido, aldehyde, caboxyl or trifluoromethyl and $R_3$ comprises hydrogen, halogen, hydroxy alkyl, amino, nitro, cyano, trifluoromethyl, lower alkylsulfonyl, sulfonamide, aldehyde, alkyl carbonyl, aralkylidene carbonyl or carboxyl or a group selected from

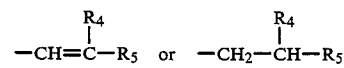

wherein $R_4$ comprises hydrogen, alkyl, cyano, carboxyl or acyl and $R_5$ comprises hydrogen, cyano, carboxyl, alkoxycarbonyl, carboxyalkenyl, nitro, acyl, optionally substituted aroyl or heteroaroyl, hydroxyalkyl or carboxyalkyl or $R_4$ and $R_5$ together form a five to seven membered substituted cycloalkanone ring;

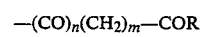

wherein n is 0–1 and m is 0–7 and R comprises hydroxy, alkyl, carboxyalkyl, optionally substituted alkene, alkoxy or optionally substituted amino;

(Abstract continued on next page.)

3OMD CONCENTRATION IN SERUM
●——— Compound of Example 5
○----- Control

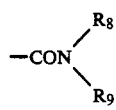
wherein $R_8$ and $R_9$ independently comprise hydrogen or one of the following optionally substituted groups; alkyl, alkenyl, alkynyl, cycloalkyl, aralkyl, or together form an optionally substituted piperidyl group;
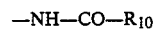
wherein $R_{10}$ comprises a substituted alkyl group.
14 Claims, 2 Drawing Sheets

PHARMACOLOGICALLY ACTIVE COMPOUNDS, METHODS FOR THE PREPARATION THEREOF AND COMPOSITIONS CONTAINING THE SAME

The present invention relates to new pharmacologically active catechol derivatives according to formula I

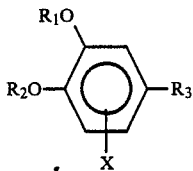

wherein $R_1$ and $R_2$ independently comprise hydrogen, alkyl, optionally substituted acyl or aroyl, lower alkylsulfonyl or alkylcarbamoyl or taken together form a lower alkylidene or cycloalkylidene group, X comprises electronegatives substituent such as halogen, nitro, cyano, lower alkylsulfonyl, sulfonamido, trifluoromethyl, aldehyde or carboxyl and $R_3$ comprises hydrogen, halogen, substituted alkyl, cyano, hydroxyalkyl, nitro, optionally substituted amino, trifluoromethyl, lower alkylsulfonyl, sulfonamido, aldehyde, alkyl carbonyl, aralkylidene carbonyl or carboxyl group or a group selected from

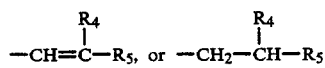

wherein $R_4$ comprises hydrogen, alkyl, amino, cyano, carboxyl or acyl and $R_5$ comprises hydrogen, amino, cyano, carboxyl, alkoxycarbonyl, carboxyalkenyl, nitro, acyl, hydroxyalkyl, carboxyalkyl or one of optionally substituted groups; carboxamido, carbamoyl, aroyl or heteroarcyl or $R_4$ and $R_5$ together form a five to seven membered substituted cycloalkanone ring;

wherein n is 0-1, m is 0-7 and R comprises alkyl, hydroxy, carboxyalkyl, optionally substituted alkene, alkoxy or substituted amino;

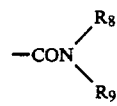

wherein $R_8$ and $R_9$ independently comprise hydrogen or one of the following optionally substituted groups; alkyl, alkenyl, alkynyl, cycloalkyl, aralkyl or taken together form an optionally substituted piperidyl group;

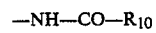

wherein $R_{10}$ comprises a substituted alkyl group.

The term "alkyl" is employed herein by itself or as part of another group includes both straight and branched chain radicals of up to 18 carbon atoms, preferably 1 to 8 carbon atoms, most preferably 1 to 4 carbon atoms. The term "lower alkyl" as employed herein by itself or as part of another group includes both straight and branched chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, hexyl, octyl, decyl and dodecyl including the various branched chain isomers thereof.

The term "alkenyl" and "alkynyl" designate a hydrocarbon residue as defined above with respect to the term "alkyl" including at least one carbon to carbon double bond and carbon to carbon triple bond, respectively. The alkenyl and alkynyl residues may contain up to 12, preferably 1 to 8, most preferably 1 to 4 carbon atoms.

The term "acyl" as employed herein by itself or as part of another group refers to an alkylcarbonyl or alkenylcarbonyl group, the alkyl and alkenyl groups being defined above.

The term "aroyl" as used herein by itself or as part of another group refers to an arylcarbonyl group, the aryl group being a monocyclic or bicyclic group containing from 6 to 10 carbon atoms in the ring portion. Specific examples for aryl groups are phenyl, naphtyl, and the like.

The term "lower alkylidene" refers to a chain containing from 2 to 8, preferably 2 to 4 carbon atoms. In a similar way the term "cycloalkylidene" refers to a cyclic hydrocarbon group containing 3 to 8, preferably 5 to 7 carbon atoms.

The term "alkoxy" as employed herein by itself or as part of another group includes an alkyl residue as defined above linked to an oxygen atom.

The term "cycloalkyl" includes saturated cyclic hydrocarbon groups containing 3 to 8, preferably 5 to 7 carbon atoms. Specific examples are the cyclopentyl, cyclohexyl, cycloheptyl and adamantyl groups.

The term "aralkyl" as employed herein refers to alkyl groups as defined above having an aryl substituent. A specific example is the benzyl group.

The term "halogen" as used herein refers to chlorine, bromine, fluorine or iodine, chlorine and bromine being preferred.

The term "optionally substituted" as used herein in connection with various residues refers to halogen substituents, such as fluorine, chlorine, bromine, iodine or trifluoromethyl groups, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The term "optionally substituted" groups may contain 1 to 3, preferably 1 or 2, most preferably 1 of the above mentioned substituents.

The term "heteroaroyl" or "heteroaryl" or "heteroalkyl" as employed herein refers to monocyclic or bicyclic group containing 1 to 3, preferably 1 or 2 heteroatoms N and/or O and/or S. Specific examples are morfolinyl, piperidyl, piperidinyl, piperazinyl, pyridyl, pyrrolyl, quinolinyl and quinolyl.

The invention also relates to pharmaceutically acceptable salts of the present compounds.

The present invention also relates to methods for the preparation of compounds of formula I. In accordance with the present invention compounds of formula I may be prepared for instance so, that an aldehyde of formula II

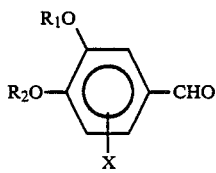

wherein $R_1$, $R_2$ and $X$ are as defined above, is condensed in a base or acid catalyzed reaction with a compound of formula III

having an active methyl or methylene group and wherein $R_4$ and $R_5$ are as defined above, giving the compounds of formula Ia

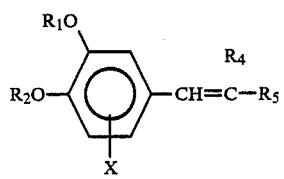

wherein $R_4$ and $R_5$ are as defined above and wherefrom the double bond optionally may be reduced to a single bond.

The compounds according to formula II are also, in addition to being valuable medicines according to the present invention, new valuable intermediates for preparing other valuable products according to the invention.

Compounds of formula II wherein X is a cyano group can be prepared from the corresponding compounds, wherein X is halogen, preferably bromine, by allowing these compounds to react with cuprous cyanide in a polar, aprotic solvent, such as pyridine, N-methylpyrrolidone or N,N-dialkylformamide at elevated temperature (100°–200° C.).

Alternatively the compounds of formula II, wherein X is a 5-cyano group can be prepared by formylation of 2,3-dihydroxybenzonitrile with hexamethylenetetramine.

Compounds of formula II, wherein X is 5-trifluoromethyl can be prepared starting from 3-methoxytrifluoromethylbenzene of formula XIV

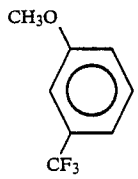

which compound is treated first with butyllithium and then with trimethylborate and further with performic acid to give the compound of formula XV

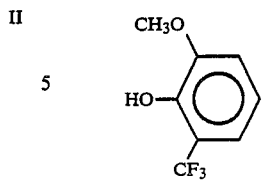

which compound is formylated with hexamethylenetetramine in trifluoroacetic acid to give a compound of formula XVI

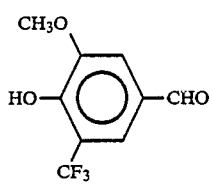

which compound is, if desired, demethylated for example with boron tribromide to give the compound of formula XVII

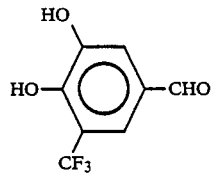

Compounds of formula II, wherein X comprises a 5-methylsulfonyl group, can be prepared from 2,3-dimethoxythioanisole of the formula XVIII

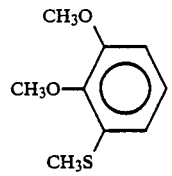

which compound is treated first for example with peroxyacetic acid to give the corresponding sulfone of formula XIX

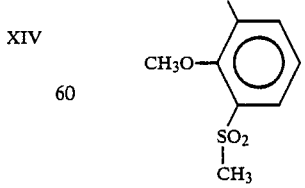

which compound is then formylated with hexamethylenetetramine in trifluoroacetic acid to give the compound of formula XX

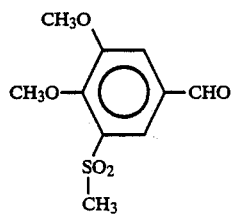
XX which compound may be, if desired, demethylated (HBr or BBr₃) to give a compound of formula XXI

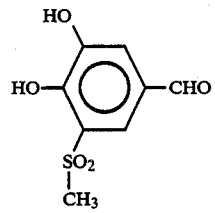
XXI

The compound of formula II, wherein X comprises sulfonamido, can be prepared by formylation of 2,3-dihydroxybenzenesulfonamide of formula XXII

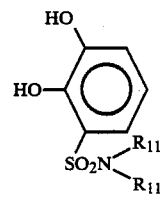
XXII wherein $R_{11}$ means hydrogen or alkyl, to give the compound of formula XXIII

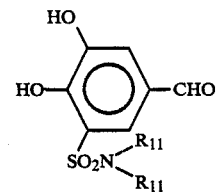
XXIII

Alternatively compounds of formula I according to the present invention can be prepared from a ketone of formula IV

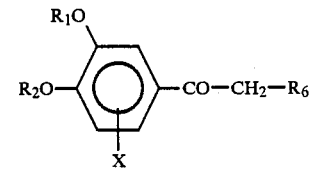
IV wherein $R_1$, $R_2$, X are as defined above and $R_6$ comprises hydrogen or alkyl, by a condensation with an aldehyde of formula V

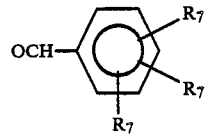
V wherein $R_7$ comprises hydrogen, alkyl, alkoxy or dialkylamino to give the compounds of formula Ib

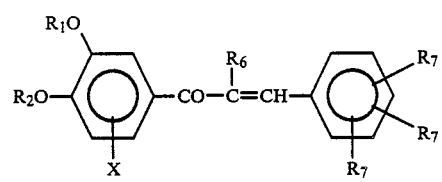
Ib wherein $R_1$, $R_2$, X, $R_6$ and $R_7$ are as defined above.

Alternatively compounds of formula I, wherein $R_3$ comprises a substituted alkyl group can be prepared by Friedel-Craft's reaction from a compound of formula VI

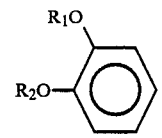
VI wherein $R_1$ and $R_2$ are as defined above by allowing the compound of the formula VI to react in the presence of aluminium chloride either with a cyclic acid anhydride of formula VII

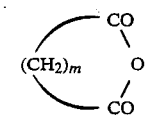
VII wherein m is 1–7 or alternatively with a dicarboxylic acid ester chloride of formula VIII

Hal—(CO)ₙ—(CH₂)ₘ—COR    VIII wherein m is 0–7 and n is 0–1 and R is as defined above and Hal is a halogen atom, to give the compounds of formula IX

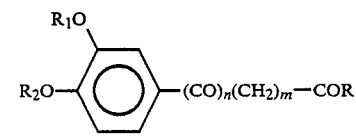
IX wherein the aromatic ring will be substituted with the group X to give the compounds of formula Ic

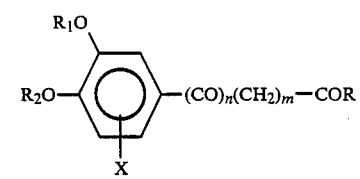
Ic wherein R, R₁, R₂ and X are as defined above.

In the compounds of formula Ic the carbonyl group can be reduced to a methylene group by conventional methods (Clemmensen and Wolff-Kischner reduction) to give compounds of formula Id

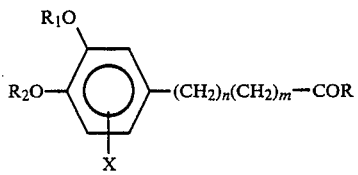

Id

The compounds according to the present invention, wherein R₃ comprises a substituted carbamido group, can be prepared by allowing an activated benzoic acid derivative of formula X

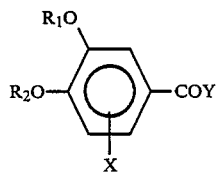

X wherein R₁, R₂ and X are as defined above and Y comprises halogen or some other activated group to react with an amine of formula XI

XI wherein R₈ and R₉ are as defined above to give compounds of formula Ie

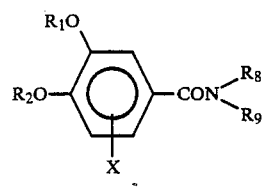

Ie wherein R₁, R₂, X, R₈ and R₉ are as defined above.

The compounds of formula I, wherein R₃ is an acylated amino group having formula If

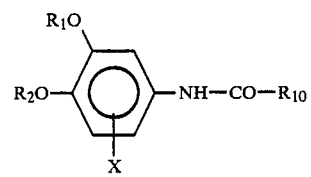

If wherein R₁, R₂, X and R₁₀ are as defined above can be prepared by allowing an aniline derivative of formula XII

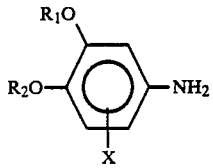

XII wherein R₁, R₂ and X are as defined above, to react with an activated carboxylic acid derivative of formula XIII $$Y-CO-R_{10}$$  XIII wherein Y and R₁₀ are as defined above.

The invention also relates to compositions where the compounds of formula I may be used as the active medicine. The compositions may contain the compounds of formula I alone or combined with some other medicines. For the treatment of Parkinson's disease the compounds according to formula I are given with levodopa, each in its own composition or combined in one composition. Also peripheral dopa decarboxylase (DDC) inhibitors, such as carbidopa or benserazide may be present, even though they are not obligatory.

The compounds according to this invention may be given in different dosage forms for administering in any suitable enteral or parenteral way. The dosage forms, like tablets, pills, injection liquids etc may be manufactured by the known principles in the art. One can use any pharmaceutically accepted additives, carrier, lubricants, fillers etc to modify different properties of the dosage forms.

Catechol-O-methyltransferase (COMT) catalyzes the transfer of the methyl group from S-adenosyl-L-methionine to a number of compounds with catechol structures. This enzyme is important in the extraneuronal inactivation of catecholamines and drugs with catechol structures. COMT is one of the most important enzymes involved in the metabolism of catecholamines. It is present in most tissues, both in the periphery and the central nervous system. The highest activities are found in the liver, intestine and kidney. COMT probably is present in soluble and membrane bound forms. The exact character of the two forms has not been established.

In Parkinson's disease the dopaminergic neurones, primarily the nigrostriatal neurones, are damaged, causing dopamine deficiency in the cerebral basal ganglia. This deficiency can be compensated by levodopa which is converted to dopamine in the central nervous system under the influence of DDC.

Today, levodopa treatment is almost invariably supplemented with a peripheral DDC inhibitor to inhibit too early dopamine formation and thereby to increase the cerebral levodopa concentration and to decrease the peripheral side effects of dopamine.

In addition to DDC, COMT metabolizes levodopa, converting it to 3-O-methyldopa (3-OMD). 3-OMD readily penetrates the blood-brain barrier via an active transport system. Alone it is therapeutically ineffective and detrimental when competing with levodopa. 3-OMD is accumulated in tissues because of its long half-life (ca. 15 h) compared to levodopa (ca. 1 h). The high activity of COMT clearly correlates with the poor efficacy of levodopa despite the presence of peripheral DDC inhibitor.

In addition to monoamine oxidase (MAO), COMT is a major enzyme participating in the amine metabolism. By inhibiting the metabolism of endogenous amines (dopamine, noradrenaline, adrenaline) in the brain the COMT inhibitors decrease decomposition of these compounds. Thus they may be useful in the treatment of depression.

By inhibiting peripheral COMT effectively, COMT inhibitors direct the metabolic route of levodopa towards decarboxylation, forming thereby more dopamine which is important in the treatment of hypertension and heart failure.

It has been unexpectedly observed that the compounds according to the invention are extremely effective COMT inhibitors. They open up new, previously unknown possibilities in the treatment of Parkinson's disease. In addition the new compounds may be useful also in the treatment of depression and heart failure as well as hypertension.

The new COMT inhibitors, which inhibit formation of 3-OMD, may decrease the adverse effects of long-term use of levodopa. Furthermore, levodopa doses can be reduced. It has been shown that the dose of levodopa can be reduced by half or to one-third of the dose used without COMT inhibitor. Since dosage of levodopa is individual, it is difficult to give any absolute dosage, but daily doses as low as 25-50 mg have been considered sufficient to start with.

A preliminary clinical trial on n-butyl gallate, a known COMT inhibitor, showed patients with Parkinson's disease clearly to benefit of n-butyl gallate. The study was, however, discontinued because of the too high toxicity of n-butyl gallate.

The COMT inhibitory efficacy of the compounds according to the invention was tested using the following experimental procedures.

Determination of COMT activity in vitro The in vitro activity of COMT was determined in enzyme preparations isolated from the brain and liver of female Han:WIST rats, weight ca. 100 g. The rats were killed by carbon dioxide, and the tissues were removed and stored at $-80°$ C. until determination of enzyme activity.

The enzyme preparation was prepared by homogenizing the tissues in 10 mM phosphate buffer, pH 7.4, (1:10 weight g/ml) which contained 0.5 mM dithiotreitol. The homogenate was centrifuged 15,000×G for 20 min. The supernatant was recentrifuged 100,000×G for 60 min. All procedures were done at $+4°$ C. The supernatant of the last centrifugation (100000×G) was used to determine the activity of soluble COMT enzyme.

Determination of $IC_{50}$ was performed by measuring the COMT activity in several drug concentrations of the reaction mixture which contained the enzyme preparation, 0.4 mM dihydroxybenzoic acid (substrate), 5 mM magnesium chloride, 0.2 mM S-adenosyl-L-methionine and COMT inhibitor in 0.1 M phosphate buffer, pH 7.4. No COMT inhibitor was added to the control. The mixture was incubated for 30 min at 37° C. whereafter the reaction was stopped by perchloric acid and the precipitated proteins were removed by centrifugation (4000×G for 10 min). The activity of the enzyme was measured by determining the concentration of 3-methoxy-4-hydroxybenzoic acid formed from the substrate of COMT (dihydroxybenzoic acid) by HPLC using an electrochemical detector. Chromatography was performed by injecting 20 μl of the sample in a 4.6 mm×150 mm Spherisorb ODS column (particle size 5 μm). The reaction products were eluted from the column with 20% methanol containing 0.1 M phosphate, 20 mM citric acid and 0.15 mM EDTA, pH 3.2, at a flow rate of 1.5 ml/min. The electrochemical detector was set to 0.9 V against an Ag/AgCl electrode. The concentration of the reaction product, 3-methoxy-4-hydroxybenzoic acid, was compared with the control samples and the samples containing COMT inhibitor. The $IC_{50}$ value is the concentration which causes a 50% decrease in COMT activity.

Effect of COMT inhibitors in vivo

Male Han:WIST rats, weight 200-250 g, were used in the experiment. The control group was given 50 mg/kg carbidopa 30 min before levodopa (50 mg/kg). The test group was also given carbidopa 50 mg/kg 30 min before levodopa+COMT inhibitor. The drugs were administered orally.

Sampling

About 0.5 ml of blood was drawn from the tail artery. The sample was allowed to coagulate in ice. Thereafter the sample was centrifuged and serum separated. Serum was stored at $-80°$ C. until determination of concentrations of levodopa and its metabolite 3-OMD.

Determination of levodopa and 3-OMD serum concentrations

To serum (e.g. 100 μl), an equal volume of 0.4 M perchloric acid, 0.1% sodium sulphate, 0.01% EDTA, which contained dihydroxybenzylamine as internal standard, were added. The sample was mixed and kept in ice, whereafter the proteins were removed by centrifugation (4000×G for 10 min.) and the concentrations of levodopa and 3-OMD were determined by HPLC using an electrochemical detector. The compounds were separated in a 4.6 mm×150 mm Ultrasphere ODS column in an eluent containing 4% acetonitrile, 0.1 M phosphate buffer, 20 mM citric acid, 0.15 mM EDTA, 2 mM octylsulphonic acid and 0.2% tetrahydropholan, pH 2.8. The flow rate was 2 ml/min.

The electrochemical detector was set to $+0.8$ V against an Ag/AgCl electrode. The concentrations of the test compounds were determined by comparing the heights of the peaks with that of the internal standard. The ratio was used to calculate the serum concentrations of levodopa and 3-OMD in control rats and those given COMT inhibitor.

Results

The best COMT inhibitors according to the invention were more than thousand times more potent in vitro than the most potent known reference compound U-0521 (Table I). Also the orally administered COMT inhibitors were shown to inhibit the formation of serum 3-OMD significantly more than U-0521 (Table II). The reference compound U-0521 furthermore penetrated the blood-brain barrier and inhibited the thyrosine hydroxylase activity thereby blocking the biosynthesis of vitally important catecholamines. In contrast the compounds according to the invention are COMT specific and they do not significantly penetrate the blood-brain barrier.

Results in vitro

TABLE 1

(structure: benzene ring with $R_1O$, $R_2O$, $R_3$, and $X$ substituents)

| Example compound | $R_1$ | $R_2$ | X | $R_3$ | COMT-INHIBITION IN BRAIN TISSUE (IC50(nM)) |
|---|---|---|---|---|---|
| 79 | H | H | 5-$NO_2$ | (2,5-bis-arylidenecyclopentanone with 3,4-dihydroxy-5-nitrophenyl group): $CH=$ (cyclopentanone) $=CH$—(3,4-dihydroxy-6-nitrophenyl) | 3 |
| 11 | H | H | 5-$NO_2$ | $CH=CH-\underset{\underset{O}{\|}}{C}$—(3,4,5-trimethoxyphenyl) | 5 |
| 8 | H | H | 5-$NO_2$ | $CH=CH-\underset{\underset{O}{\|}}{C}$—phenyl | 6 |
| 6 | H | H | 5-$NO_2$ | $CH=\underset{\underset{CH_3}{\|}}{C}-\underset{\underset{O}{\|}}{C}-CH_3$ | 12 |
| 110 | H | H | 5-$NO_2$ | $NO_2$ | 12 |
| 109 | H | H | 5-$NO_2$ | $\underset{\underset{O}{\|}}{C}-CH_3$ | 16 |
| 130 | $CH_3(CH_2)_2\underset{\underset{O}{\|}}{C}$ | H | 5-$NO_2$ | $NO_2$ | 18 |
| 5 | H | H | 5-$NO_2$ | $CH=C\underset{CN}{\overset{CN}{\diagup}}$ | 20 |
| 27 | H | H | 5-$NO_2$ | $CH_2CH_2CH_2CH_2CON\underset{\underset{CH_3}{\|}}{}-CH_2C\equiv CH$ | 20 |
| 16 | H | H | 5-$NO_2$ | $CH=\underset{\underset{CH_3}{\|}}{C}-\underset{\underset{OH}{\|}}{CH}-CH_3$ | 23 |
| 111 | H | H | 5-$NO_2$ | $\underset{\underset{O}{\|}}{C}-H$ | 24 |
| 113 | H | H | 5-$NO_2$ | Cl | 25 |
| 112 | H | H | 5-$NO_2$ | CN | 30 |
| 28 | H | H | 5-$NO_2$ | $CH_2CH_2CH_2CH_2CONH$—(adamantyl) | 27 |
| 26 | H | H | 5-$NO_2$ | $CH_2CH_2CH_2CH_2CONH-CH\underset{CH_3}{\overset{CH_3}{\diagup}}$ | 33 |
| 3 | H | H | 5-$NO_2$ | $CH=CH-COOH$ | 37 |

TABLE 1-continued $$\text{structure: benzene ring with } R_1O, R_2O, R_3, X \text{ substituents}$$

| Example compound | $R_1$ | $R_2$ | X | $R_3$ | COMT-INHIBITION IN BRAIN TISSUE (IC50(nM)) |
|---|---|---|---|---|---|
| 128 | $CH_3CH_2C(=O)$ | $CH_3CH_2C(=O)$ | 5-$NO_2$ | $NO_2$ | 60 |
| 127 | $CH_3-C(=O)$ | $CH_3-C(=O)$ | 5-$NO_2$ | $NO_2$ | 75 |
| 24 | H | H | 5-$NO_2$ | $CH_2CH_2CH_2CH_2COOH$ | 90 |
| 109 | H | H | 5-$NO_2$ | H | 140 |
| 131 | $(CH_3)_3C-C(=O)$ | H | 5-$NO_2$ | $NO_2$ | 220 |
| 41 | H | H | 6-$NO_2$ | $CH_2CH_2CH_2CH_2COOH$ | 380 |
| 54 | H | H | 5-Cl | CONH-adamantyl | 400 |
| 67 | $CH_3CO$ | $CH_3CO$ | 6-$NO_2$ | CO-N-piperidinyl-CO-cyclohexyl | 750 |
| U-0521 | H | H | 5-H | $COCH(CH_3)_2$ | 6000 |

TABLE 2

In vivo results

| Oral dose | Compound | 3-OMD concentration % of control | |
|---|---|---|---|
| | | 1 h | 5 h |
| 3 mg/kg | Example 110 | −97 | −80 |
| 4.3 mg/kg | Example 127 | −67 | −76 |
| 4.7 mg/kg | Example 128 | −70 | −77 |
| 4.3 mg/kg | Example 131 | −92 | −83 |
| 4.1 mg/kg | Example 130 | −98 | −92 |
| 30 mg/kg | Example 19 | −99 | −76 |
| 30 mg/kg | Example 111 | −100 | −65 |
| 30 mg/kg | Example 5 | −96 | −89 |
| 30 mg/kg | Example 6 | −84 | −49 |
| 30 mg/kg | Example 11 | −63 | −26 |
| 30 mg/kg | Example 8 | −58 | −34 |
| 100 mg/kg | Example 24 | −86 | −41 |
| 100 mg/kg | U-0521 | −34 | −14 |

The results indicate that the compounds according to the invention are even more than thousand times more potent in vitro (Table 1) than the reference compound (U-0521). The orally administered new compounds inhibit COMT also in vivo significantly better than the reference compound, which is reflected as decreased serum 3-OMD concentration (Table 2). The reference compound U-0521 furthermore penetrates the blood-brain barrier and nonspecifically inhibits thyrosine hydroxylase which is essential for the biosynthesis of catecholamines.

FIG. 1 shows the 3-OMD serum concentrations for the new compound (e.g. according to example 5) and for the control compound which does not contain COMT inhibitor. The experimental design is the same as for the in vivo experiments above.

Figure 2:
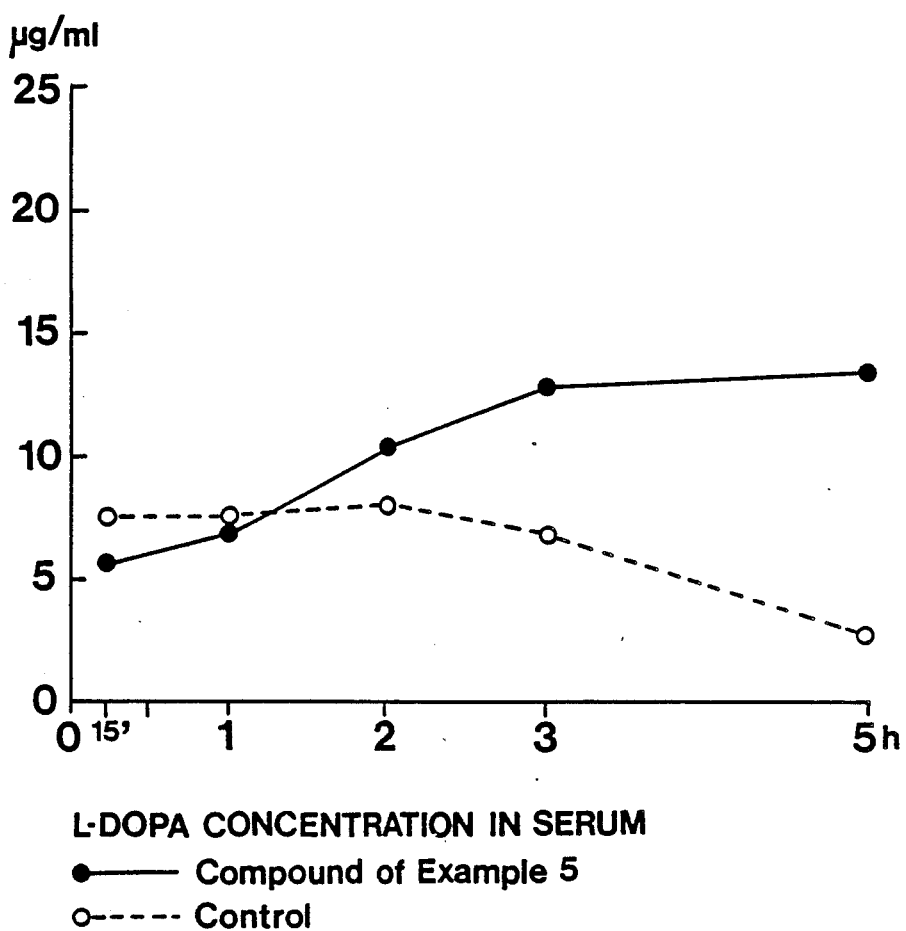

FIG. 2 shows the levodopa serum concentrations after the same treatments. These figures show that the compounds according to the invention increase the bioavailability of levodopa and decrease the level of the harmful metabolite 3-OMD. The change observed in serum is reflected in the brain concentrations of 3-OMD and levodopa.

Specificity of COMT inhibition

The new compounds are specifically COMT inhibitors and not inhibitors of other essential enzymes. This was shown in in vitro experiments which were performed as described above.

| Compound | IC$_{50}$ (nM) | | | | | |
| --- | --- | --- | --- | --- | --- | --- |
| | COMT | TH | DBH | DDC | MAO-A | MAO-B |
| Example 87 | 3 | 38.000 | >50.000 | >50.000 | >50.000 | >50.000 |
| Example 11 | 5 | 18.000 | >50.000 | >50.000 | >50.000 | >50.000 |
| Example 8 | 6 | 21.000 | >50.000 | >50.000 | >50.000 | >50.000 |
| Example 6 | 12 | 50.000 | >50.000 | >50.000 | >50.000 | >50.000 |
| Example 110 | 12 | 14.000 | >50.000 | >50.000 | >50.000 | >50.000 |
| Example 19 | 16 | 17.500 | >50.000 | >50.000 | >50.000 | >50.000 |
| Example 5 | 20 | 21.000 | >50.000 | >50.000 | >50.000 | >50.000 |
| Example 111 | 24 | 50.000 | >50.000 | >50.000 | >50.000 | >50.000 |
| U-0521 | 6000 | 24.000 | >50.000 | >50.000 | >50.000 | >50.000 |

TH = Thyrosine hydroxylase,
DBH = Dopamine-β-hydroxylase
MAO-A and -B = Monoamine oxidase-A and -B.

The COMT inhibitors according to the invention are extremely specific. They inhibit COMT effectively at low concentrations, while inhibition of other enzymes involved in the metabolism of catecholamines requires a 1000–10000 times higher concentration. The difference between the inhibition of TH and COMT in the reference compound U-0521 is only 4-fold.

IC$_{50}$ is the concentration which inhibits 50% of the enzyme activity.

Toxicity

The new COMT inhibitors are non-toxic. For instance, the LD$_{50}$ of 3-(3,4-dihydroxy-5-nitrophenyl)-1-(3,4,5-trimethoxyphenyl)prop-2-en-1-one (Example 11) given as an oral suspension to rats, was over 2500 mg/kg.

EXAMPLE 1

3-Nitro-5-[2-(4-pyridyl)vinyl] catechol

A solution containing 2.0 g (0.011 mole) of 3,4-dihydroxy-5-nitrobenzaldehyde and 2.23 g (0.024 mole) of 4-picoline in 9.0 ml of acetic anhydride was refluxed for 1 h. About 15 ml of isopropanol was then added and the solution was cooled to 0° C. where upon the diacetyl-derivative of the desired product crystallized. After filtration the product was suspended in 100 ml of 0.5 N hydrochloric acid and refluxed for 1.5 h. After cooling the precipitate was filtered, washed with water and acetone and dried. Yield 1.89 g (67%), m.p. above 350° C.

EXAMPLE 2

3-Nitro-5-[2-(4-quinolyl)vinyl] catechol

The same procedure described in Example 1 was repeated using 2.0 g (0.011 mole) of 3,4-dihydroxy-5-nitrobenzaldehyde and 3.44 g (0.024 mole) of 4-quinaldine. Yield 1.7 g (50%), m.p. 250° C. (decomp.).

EXAMPLE 3

4-Hydroxy-3-methoxy-5-nitrocinnamic acid

A solution of 1.0 g of 5-nitrovanillin and 4.0 g of malonic acid in 10 ml of pyridine was heated for 50 h at 80° C. The reaction mixture was diluted with water, acidified with hydrochloric acid, filtered, washed with water and dried. Yield 0.44 g (36%). The $^1$H-NMR spectrum was in accordance with the structure alleged.

EXAMPLE 4

3,4-Dihydroxy-5,ω-dinitrostyrene

A solution containing 3.66 g (0.02 mole) of 3,4-dihydroxy-5-nitrobenzaldehyde, 3.66 g (0.06 mole) of nitromethane and 3.31 g of ammonium acetate in 10 ml of abs. ethanol was refluxed for 6 h. Water was added to the reaction mixture. The mixture was acidified with hydrochloric acid and extracted with methylene chloride. The methylene chloride extract was washed with water and the solvent was evaporated in vacuo. The residue was crystallized from isopropanol, yield 1.9 g (40%), m.p. 258°–260° C.

EXAMPLE 5

3,4-Dihydroxy-5-nitro-ω,ω-dicyanostyrene

The same procedure described in Example 4 was repeated using 3.0 g of 3,4-dihydroxy-5-nitrobenzaldehyde and 3.0 g of malonodinitrile. The product was crystallized from methanol-water, yield 1.9 g (50%), m.p. 205°–209° C.

EXAMPLE 6

4-(3,4-Dihydroxy-5-nitrophenyl)-3-methylbut-3-en-2-one

A solution containing 0.5 g of 3,4-dihydroxy-5-nitrobenzaldehyde in 2.0 ml of butanone was saturated with gaseous hydrogen chloride. After standing over night ether was added to the solution and it was filtered. The product was crystallized from isopropanol, yield 0.2 g (30%), m.p. 139°–141° C.

EXAMPLE 7

3-(3,4-Dihydroxy-5-nitrobenzylidene)-2,4-pentanedione

A solution containing 1.83 g of 3,4-dihydroxy-5-nitrobenzaldehyde and 1.00 g of 2,4-pentanedione in 10 ml of tetrahydrofuran was saturated with gaseous hydrogen chloride. After standing over night at 5° C. the product was filtered and washed with ether. Yield 1.2 g (50%), m.p. 175°–178° C.

EXAMPLE 8

3-(3,4-Dihydroxy-5-nitrophenyl)-1-phenylprop-2-en-1-one

A solution containing 0.55 g of 3,4-dihydroxy-5-nitrobenzaldehyde and 0.36 g of acetophenone in 10 ml of methanol was saturated with gaseous hydrogen chloride. After standing over night at 5° C. the product was filtered and washed with methanol. Yield 0.55 g (68%), m.p. 192°–195° C.

EXAMPLE 9

3-(3,4-Dihydroxy-5-nitrophenyl)-1-(4-methoxyphenyl)-prop-2-en-1-one

The procedure described in Example 8 was repeated using 1.8 g of 3,4-dihydroxy-5-nitrobenzaldehyde and 1.5 g of 4'-methoxyacetophenone in 20 ml of tetrahydrofuran. Yield 1.88 g (60%), m.p. 222°–228° C.

EXAMPLE 10

3-(3,4-Dihydroxy-5-nitrophenyl)-1-(3,4-dimethoxyphenyl)prop-2-en-1-one

The procedure described in Example 8 was repeated using 1.8 g of 3.4-dihydroxy-5-nitrobenzaldehyde and 1.8 g of 3',4'-dimethoxyacetophenone in 20 ml of methanol. Yield 1.7 g (50%), m.p. 206°–208° C.

EXAMPLE 11

3-(3,4-Dihydroxy-5-nitrophenyl)-1-(3,4,5-trimethoxyphenyl)prop-2-en-1-one

The procedure described in Example 8 was repeated using 0.55 g of 3,4-dihydroxy-5-nitrobenzaldehyde and 0.63 g of 3',4',5'-trimethoxyacetophenone. Yield 0.50 g (44%), m.p. 213°–216° C.

EXAMPLE 12

3-(3,4-Dihydroxy-5-nitrophenyl)-1-(2-hydroxyphenyl)-prop-2-en-1-one

The procedure described in Example 8 was repeated using 1.0 g of 3,4-dihydroxy-5-nitrobenzaldehyde and 0.74 g of 2'-hydroxyacetophenone. Yield 0.2 g (12%), m.p. 231°–234° C.

EXAMPLE 13

3-(3,4-Diacetoxy-5-nitrophenyl)-1-phenylprop-2-en-1-one

A solution containing 1.0 g of the product obtained in Example 8 in 5.0 ml of acetic anhydride was refluxed for 2 h. After cooling the product was filtered and washed with ether. Yield 0.73 g (68%), m.p. 183°–185° C.

EXAMPLE 14

3-(3,4-Dibenzoyloxy-5-nitrophenyl)-1-phenylprop-2-en-1-one 1.0 g of the product obtained in Example 8 and 2.0 ml of benzoylchloride were dissolved in 5 ml of tetrahydrofuran. Tetrahydrofuran was distilled off to a great extend and the residue was refluxed for 2 h. After cooling ether was added to the mixture and the product was filtered and triturated with ethylmethylketone. Yield 0.50 g (29%), m.p. 206°–210° C.

EXAMPLE 15

3-(3-Pivaloyloxy-4-hydroxy-5-nitrophenyl)-1-phenyl-prop-2-en-1-one 1.0 g of the product obtained in Example 8 was dissolved in 5 ml of tetrahydrofuran, 4.7 ml of pivaloyl chloride was added and the mixture was refluxed for 16 h. The solvent was evaporated in vacuo and the residue was purified in a silicagel column by using toluene-acetic acid-dioxane (18:1:1) mixture as an eluent. The product was crystallized from ether, m.p. 148°–150° C.

EXAMPLE 16

4-(3,4-Dihydroxy-5-nitrophenyl)-3-methylbut-3-en-2-ol 1.8 g of the product obtained in Example 6 was dissolved in 20 ml of 1N NaOH-solution and 4.0 g of sodium borohydride in small amount of water was added. The mixture was stirred over night at room temperature, acidified with hydrochloric acid and extracted with ether. The solvent was evaporated in vacuo and the residue purified in a silica gel column by using toluene-acetic acid dioxane (18:1:1). The product was crystallized from dichloromethane petroleum ether. Yield 0.80 g (44%), m.p. 102°–104° C.

EXAMPLE 17

7-(3,4-Dihydroxy-5-nitrobenzylidene)-8-ketononanoic acid

The procedure described in Example 9 was repeated using 1.83 g of 3,4-dihydroxy-5-nitrobenzaldehyde and 1.72 g of 8-ketononanoic acid. Yield 1.85 g (55%), yellow viscous oil.

EXAMPLE 18

4'-Hydroxy-3'-methoxy-5'-nitroacetophenone

To a solution containing 40 ml of nitric acid (d=1.41) and 40 ml of water was gradually added while cooling (below 7° C.) and stirring 25.0 g of 4'-hydroxy-3'-methoxyacetophenone. After stirring for 0.5 h at 0° C. the product was filtered, washed first with diluted nitric acid (1:1) and then with water. Yield 24.0 g (75%). The $^1$H-NMR-spectrum of the product was in accordance with the structure alleged.

EXAMPLE 19

3,4'-Dihydroxy-5'-nitroacetophenone

A solution containing 19.9 g of the product obtained in Example 18 in 200 ml of acetic acid and 200 ml of 48% hydrobromic acid was refluxed for 5 h. 500 ml of a saturated solution of sodium sulfate was added to the reaction mixture and the same was let stand overnight at 5° C. The solution was extracted with ether. The ether phase was washed with 200 ml of water, dried and the solvent evaporated in vacuo. The residue was crystallized from isopropanol. Yield 10.2 g (55%), m.p. 155°–159° C.

EXAMPLE 20

1-(3,4-Dihydroxy-5-nitrophenyl)-3-(4-dimethylaminophenyl)prop-2-en-1-one

A solution containing 0.5 g of the product obtained in Example 19 and 0.38 of 4-dimethylaminobenzaldehyde in 5 ml of methanol was saturated with gaseous hydrogen chloride. The solution was refluxed for 1 h. After cooling the product was filtered and washed with methanol. Yield 0.26 g (70%), decomp. on heating.

EXAMPLE 21

5-(4-Benzyloxy-3-methoxyphenyl)-2,4-pentadienoic acid

To a solution containing 260 g of 4-benzyloxy-3-methoxybenzaldehyde and 200 ml of ethyl crotonate in 1200 ml of N-methylpyrrolidone was gradually added while stirring and cooling at 0° C. 149.6 g of potassium tert.-butoxide. The solution was stirred for 0.5 h after which 200 ml of 10 N NaOH-solution was added and stirred for 0.5 h more at 0° C. The reaction mixture was added to a mixture of hydrochloric acid and ice. The semisolid product was separated and used without purification to the next step.

EXAMPLE 22

5-(4-Hydroxy-3-methoxyphenyl)pentanoic acid

The raw product obtained in Example 21 was dissolved in 500 ml of N,N-dimethylformamide and 22 g of 10% palladium on charcoal catalyst was added. The mixture was hydrogenated at 60° C. and normal pressure until the theoretical amount (3 mole) of hydrogen was consumed. After filtering the solvent was evaporated in vacuo to a great extent and the residue was dissolved in 1 l of dichloromethane and washed with 2 l of water. The product was extracted with 1.5 l of saturated $NaHCO_3$-solution. After acidification of the aqueous phase with hydrochloric acid the product was extracted with 1 l of dichloromethane. The solvent was distilled off in vacuo and the semisolid residue (180 g) was used to the next step.

EXAMPLE 23

5-(4-Hydroxy-3-methoxy-5-nitrophenyl)pentanoic acid

The above product (180 g) was dissolved in 1 l of dichloromethane and 820 ml of 1 molar $HNO_3$-dichloromethane solution was added gradually while stirring and cooling (0°-5° C.). The solution was stirred for 10 min more at 0° C. after which water was added. The organic phase was separated and washed with water. The solvent was evaporated in vacuo and the semisolid residue was used as such to the next step.

EXAMPLE 24

5-(3,4-Dihydroxy-5-nitrophenyl)pentanoic acid

The above product obtained in Example 23 was dissolved in a mixture containing 500 ml of acetic acid and 500 ml of 48% hydrobromic acid and refluxed for 4 h. 1 l of saturated $Na_2SO_4$-solution was added to the reaction mixture and the solution was allowed to stand over night at 5° C. The product crystallized was filtered and washed with 50% acetic acid. This product was recrystallized from ethyl acetate. Yield 32 g (16%), m.p. 135°-138° C.

EXAMPLE 25

1-Benzyl-4-5-(3,4-dihydroxy-5-nitrophenyl)pentanoylpiperazine hydrochloride

A solution containing 3.0 g of the product obtained in Example 24 in 18 ml of thionyl chloride was refluxed for 10 min. The excess of thionyl chloride was evaporated in vacuo and the acid chloride formed was dissolved in 20 ml of dichloromethane. To this solution 2.1 g of 1-benzylpiperazine in 20 ml of dichloromethane was added with stirring and stirred for 0.5 h more. Ether was added to the reaction mixture and the crystals were filtered. Yield 3.55 g (73%), m.p. 85°-89° C.

EXAMPLE 26

N-Isopropyl-5-(3,4-dihydroxy-5-nitrophenyl)pentanoic amide

A solution containing 0.5 g of the product obtained in Example 24 in 2.5 ml of thionyl chloride was refluxed for 10 min. The excess of thionyl chloride was evaporated in vacuo and the residue dissolved in 25 ml of dichloromethane. To this solution 0.47 g of isopropylamine was added and the mixture was stirred for 1 h at 20° C. Dichloromethane phase was washed with 1 N hydrochloric acid and evaporated in vacuo. The residue was crystallized from toluene. Yield 0.44 g (75%), m.p. 113°-115° C.

EXAMPLE 27

N-Methyl(-N-propargyl-5-(3,4-dihydroxy-5-nitrophenyl)pentanoic amide

The procedure described in Example 26 was repeated using 0.5 g of methyl propargylamine instead of isopropylamine.

Yield 0.5 g (83%), m.p. 133°-135° C.

EXAMPLE 28

N-(1-Adamantyl)-5-(3,4-dihydroxy-5-nitrophenyl)-pentanoic amide

The procedure described in Example 26 was repeated using 1.5 g of 1-aminoadamantane instead of isopropylamine. Yield 0.61 g (80%), m.p. 157°-160° C.

EXAMPLE 29

Tetradecyl-5-(3,4-dihydroxy-5-nitrophenyl)pentanoate

The procedure described in Example 26 was repeated using 1.26 g of 1-tetradecanol instead of isopropylamine. The reaction mixture was washed with water and the solvent evaporated in vacuo. Yield 0.44 g (50%), m.p. 46°-47° C.

EXAMPLE 30

Tetradecyl 5-(3,4-diacetoxy-5-nitrophenyl)pentanoate

A solution containing 0.1 g of the product obtained in Example 29 in 2 ml of acetic anhydride was refluxed for 20 min. The solvent was evaporated in vacuo and the residue crystallized from petroleum ether (b.p. 40° C.), m.p. 52°-54° C.

EXAMPLE 31

Tetradecyl 5-(4-hydroxy-3-pivaloyloxy-5-nitrophenyl)pentanoate

The procedure described in Example 30 was repeated using 2 ml of pivaloyl chloride instead of acetic anhydride. The product was a viscous oil.

EXAMPLE 32

5-(3,4-Dimethoxy-5-chlorophenyl)-2,4-pentadienoic acid

To a solution containing 10.0 g of dimethoxy-5-chlorobenzaldehyde and 8.3 ml of ethyl crotonate in 65 ml of N-methylpyrrolidone 6.7 g of potassium tert.-butoxide was added with stirring. The solution was stirred for 0.5 h more at 20° C. and the solution was poured then to a mixture of ice and hydrochloric acid and extracted with ether. The ether extract was washed with water and extracted then with $NaHCO_3$-solution. The aqueous phase was acidified with hydrochloric acid and the semisolid product was separated and washed with water. Yield 7.3 g (55%).

EXAMPLE 33

5-(3,5-Dimethoxy-5-chlorophenyl)pentanoic acid

A solution containing 6.2 g of the above product obtained in Example 32 was dissolved in a mixture of 30 ml of acetic acid and 3 ml of conc. hydrochloric acid.

Palladium on charcoal catalyst (10% Pd) was added and the mixture was hydrogenated at normal pressure and room temperature. After filteration the solvents were evaporated in vacuo. Yield 3.2 g (55%), a viscous oil.

EXAMPLE 34

5-(3,4-Dihydroxy-5-chlorophenyl)pentanoic acid

A solution containing 3.2 g of the above product in 8 ml of acetic acid and 10 ml of 48% hydrobromic acid was refluxed for 3 h. A saturated solution of $Na_2SO_4$ in water was added to the reaction mixture. The crystallized product was filtered, washed with water and recrystallized from toluene, m.p. 99°–101° C.

EXAMPLE 35

5-(3,4-Dimethoxy-6-chlorophenyl)-2,4-pentadienoic acid

To a solution containing 10.0 g 3,4 dimethoxy-6-chlorobenzaldehyde and 8 ml of ethyl crotonate in 60 ml of N-methylpyrrolidone 6.0 g of potassium tert.-butoxide was added while stirring . The solution was stirred for 0.5 h more at 20° C. and poured then to a mixture of ice and hydrochloric acid. The solution was extracted with ether. The ether solution was washed with water and extracted with 2.5 N NaOH-solution. The aqueous phase was acidified with hydrochloric acid and the semisolid product was separated. Yield 10.8 g (81%).

EXAMPLE 36

5-(3,4-Dihydroxy-6-chlorophenyl)-2,4-pentadienoic acid

To a solution containing 0.54 g of the product obtained in Example 35 in 6 ml dichloromethane 6 ml of 1 molar boron tribromide-dichloromethane solution was added and stirred for 24 h at 20° C. The solvent was evaporated in vacuo and 2 N hydrochloric acid was added to the residue. The product was filtered and washed with water. Recrystallization from isopropanol-water yielded 0.22 g (46%) of the product desired, m.p. 203°–206° C.

EXAMPLE 37

3-(3,4-Dihydroxy-5-nitrophenyl)-1-(4-methylphenyl)-prop-2-en-1-one

A solution containing 5.49 g of 3,4-dihydroxy-5-nitrobenzaldehyde and 5.37 g of 4'-methylacetophenone in 50 ml of tetrahydrofuran was added a catalytic amount of gaseous hydrogen chloride and refluxed for 4.5 h. The solvent was evaporated in vacuo and the residue crystallized from ether-petroleum-ether, yield 1.85 g (21%), m.p. 184°–186° C.

EXAMPLE 38

5-(3,4-Dimethoxyphenyl)-5-ketopentanoic acid

A solution containing 36 g of veratrole and 30 g glutaric anhydride in 120 ml of nitrobenzene was gradually added while stirring and cooling at 0° C. to a mixture of 72 g of anhydrous aluminium chloride and 240 ml of nitrobenzene. The mixture was stirred for 1 h at 0° C. and then for 18 h at 20° C. Ice and hydrochloric acid were added to the reaction mixture. Nitrobenzene layer was separated and to this ethyl acetate was added whereupon the product crystallized. After filtering the crystals were washed with ethyl acetate. Yield 42.3 g (64%).

EXAMPLE 39

5-(3,4-Dimethoxyphenyl)pentanoic acid

A mixture containing 37.6 g of the product obtained in Example 38 and 64 g of zinc turnings (treated with a solution of $HgCl_2$), 55 ml of toluene and 220 ml of conc. hydrochloric acid was refluxed for 1 h. Toluene phase was separated and evaporated in vacuo. The residue was crystallized from toluene-petroleum ether, yield 11.5 g (32%).

EXAMPLE 40

5-(3,4-Dimethoxy-6-nitrophenyl)pentanoic acid 15.0 g of product described in Example 39 was gradually added to 75 ml of nitric acid (d=1.41) at 20° C. The mixture was stirred for 20 min more. Ice-water was added and solution was extracted with dichloromethane. The solvent was evaporated in vacuo yielding 14.0 g (79%) of the desired product.

EXAMPLE 41

5-(3,4-Dihydroxy-6-nitrophenyl)pentanoic acid

A solution containing 42.0 g of the product obtained in Example 40 in 100 ml of acetic acid and 150 ml of 48% hydrobromic acid was refluxed for 10 h. 1 l of saturated $Na_2SO_4$-solution was added to the reaction mixture and extracted with ether. The solvent was evaporated in vacuo and the residue crystallized from ethyl acetate-petroleum ether. Yield 7.9 g (19%), m.p. 111°–114° C.

EXAMPLE 42

3-(3,4-Dimesyloxy-5-nitrophenyl)-1-phenylprop-2-en-1-oni

A solution containing 2.0 g of product described in Example 2 and 5 ml of mesyl chloride in 20 ml of N-methylpyrrolidone was heated for 1.5 h at 100° C. After cooling water was added and the solution was extracted with ether. The solvent was evaporated in vacuo and the residue was crystallized from 1-propanol. Yield 0.14 g, m.p. 181°–184° C.

EXAMPLE 43

N-(1-Adamantyl)-3,4-diacetoxy-5-nitrobenzamide.

A solution containing 0.85 g of 3,4-diacetoxy-5-nitrobenzoic acid and 0.32 ml of thionyl chloride and a catalytic amount of N,N-dimethylformamide in 10 ml of toluene was heated for 1 h at 80° C. The solvent was evaporated in vacuo and the residue was dissolved in 5 ml of dichloromethane and added to a mixture containing 0.56 g of 1-aminoadamantane hydrochloride and 0.94 ml of triethylamine in 10 ml of dichloromethane and stirred for 15 min at 0° C. and then 15 min at 20° C. Water was added to the reaction mixture and dichloromethane phase was separated. The solvent was evaporated in vacuo yielding yellow viscous oil 1.2 g (100%).

EXAMPLE 44

N-(1-Adamantyl)-3,4-dihydroxy-5-nitrobenzamide

A solution containing 1.2 g of the product obtained in Example 43 and a catalytic amount of sulfuric acid in 10 ml of methanol was refluxed for 3 h. 20 ml of water was added and on cooling 0.85 g (89.5%) of the desired product was crystallized, m.p. 207°–208° C.

EXAMPLE 45

4-Cyclohexylcarbonyl-1-(3,4-diacetoxy-5-nitrobenzoyl)piperidine

The procedure described in Example 43 was repeated using 0.58 g of cyclohexylcarbonylpiperidine and 0.38 ml 2,6-lutidine instead of 1-aminoadamantane hydrochloride and triethylamine respectively. Yield 1.2 g (87%), a viscous yellow oil.

EXAMPLE 46

4-Cyclohexylcarbonyl-1-(3,4-dihydroxy-5-nitrobenzoyl)piperidine

The procedure described in Example 44 was repeated using 1.2 g of the product obtained in Example 45. Yield 0.5 g (50%), m.p. 155°–165° C.

EXAMPLE 47

N-Benzyl-3,4-diacetoxy-5-nitrobenzamide 0.75 g of 3,4-diacetoxy-5-nitrobenzoic acid was converted to the corresponding acid chloride as described in Example 43. It was dissolved in 5 ml of dichloromethane and added to a solution containing 0.27 ml of benzylamine and 0.5 ml of 2,6-lutidine in 7 ml of dichloromethane. Yield 0.95 g (96%), a viscous oil.

EXAMPLE 48

N-Benzyl-3,4-dihydroxy-5-nitrobenzamide

The procedure described in Example 44 was repeated using 0.95 g of the product obtained in Example 47. Yield 0.5 g (68%), m.p. 185°–189° C.

EXAMPLE 49

N-(1-Adamantyl)-3,4-cyclohexylidenedioxy-6-nitrobenzamide 2 g of 3,4-cyclohexylidenedioxy-6-nitrobenzoic acid was converted to the corresponding acid chloride as described in Example 43. It was added to a solution containing 1.1 g of 1-aminoadamantane and 1.1 ml of triethylamine in 15 ml of dichloromethane. Yield 2.9 g (98%), a viscous oil.

EXAMPLE 50

N-(1-Adamantyl)-3,4-dihydroxy-6-nitrobenzamide

A solution containing 0.5 g of the product obtained in Example 49 and 0.09 ml of methanesulfonic acid in 8 ml of 98% formic acid was heated for 15 min at 60° C. The solvent was evaporated in vacuo and water was added to the residue. Yield 0.35 g (88%), m.p. 250°–255° C.

EXAMPLE 51

N-(4-Morpholinoethyl)-3,4-cyclohexylidenedioxy-6-nitrobenzamide 2.0 g of 3,4-cyclohexylidenedioxy-6-nitrobenzoic acid was converted into the corresponding acid chloride like described in Example 43. It was added to a solution containing 0.9 ml of 4-(2-aminoethyl)morpholine and 1.1 ml of triethylamine in 15 ml of dichloromethane. Yield 2.5 g (89%), a viscous oil.

EXAMPLE 52

N-(4-Morpholine ethyl)-3,4-dihydroxy-6-nitrobenzamide hydromesylate

The procedure described in Example 50 was repeated using 1.95 g of the product obtained in Example 51. Yield 0.8 g (40%), a viscous oil. The $^1$H-NMR-spectrum was in accordance with the alleged structure.

EXAMPLE 53

N-(1-Adamantyl)-3,4-diacetoxy-5-chlorobenzamide 0.7 g of 3,4-diacetoxy-5-chlorobenzoic acid was converted to the corresponding acid chloride and the procedure described in Example 43 was repeated. Yield 1.0 g (95%), a viscous oil.

EXAMPLE 54

N-(1-Adamantyl)-3,4-dihydroxy-5-chlorobenzamide

The product of Example 53 was deacetylated like described in Example 44. Yield 0.6 g (78%), m.p. 244°–247° C.

EXAMPLE 55

N-(1-Adamantyl)-3,4-cyclohexylidenedioxy-6-chlorobenzamide 0.8 g of 3,4-cyclohexylidenedioxy-6-chlorobenzoic acid was converted to the corresponding acid chloride and the procedure described in Example 43 was repeated. Yield 1.0 g (83%), viscous oil.

EXAMPLE 56

N-(1-Adamantyl)-3,4-dihydroxy-6-chlorobenzamide 1.0 g of the product obtained in Example 55 was treated with methanesulfonic acid in formic acid as described in Example 50. Yield 0.65 g (81%), m.p. 225°–230° C.

EXAMPLE 57

N-(1-Adamantyl)-3,4-diacetoxy-5-cyanobenzamide 0.6 g of 3,4-diacetoxy-5-cyanobenzoic acid was converted to the corresponding acid chloride and the procedure described in Example 43 was repeated. Yield 0.75 g (88%), viscous oil.

EXAMPLE 58

N-(1-Adamantyl)-3,4-dihydroxy-5-cyanobenzamide 0.75 g of the above product was deacetylated as described in Example 44. Yield 0.5 g (89%), m.p. 253°–255° C.

EXAMPLE 59

1-Butyl 3,4-dihydroxy-5-cyanobenzoate

A solution containing 0.5 g of 3,4-dihydroxy-5-cyanobenzoic acid in 10 ml of 1-butanol was saturated with gaseous hydrogen chloride at 0° C. The solution was then heated for 3 h at 100° C. The solvent was evaporated in vacuo and dichloromethane was added to the residue. The formed crystals were filtered. Yield 0.19 g (30%), m.p. 135°–140° C.

EXAMPLE 60

ω-(2-Methylpiperidyl)-3,4-dimethoxy-6-cyanopropionanilide

A mixture containing 2.68 g of ω-chloro-3,4-dimethoxy-6-cyanopropionanilide, 1.5 g of 2-methylpiperidine, 1.4 g of CaO and a catalytic amount of potassium iodide in 15 ml of toluene was heated for 18 h at 100° C. The solution was filtered, washed with water and evaporated in vacuo. The residue was treated with petroleum ether and filtered. Yield 2.79 g (84%), m.p. 126°–127° C.

Example 61

ω-(1-Adamantylamino)-3,4-dimethoxy-6-cyanopropionanilide

A mixture containing 3.0 g of ω-chloro-3,4-dimethoxy-6-cyanopropionanilide, 2.3 g of 1-aminoadamantane hydrochloride, 4.6 g of potassium carbonate and a catalytic amount of potassium iodide in 15 ml of toluene was heated while stirring for 6 h at 100° C. The solution was filtered and the solvent evaporated in vacuo. Water was added to the residue and the product was filtered. Yield 3.4 g (74%), m.p. 137°–140° C.

EXAMPLE 62

1-(3,4-Cyclohexylidenedioxy-6-nitrobenzoyl)-4-cyclohexylcarbonylpiperidine 0.5 g of 3,4-cyclohexylidenedioxy-6-nitrobenzoic acid was converted to the corresponding acid chloride as described in Example 43. It was added to a solution containing 0.35 g of 4-cyclohexylcarbonylpiperidine and 0.2 g of triethylamine in 30 ml of dichloromethane. Yield 0.7 g (85%), m.p. 270° C.

EXAMPLE 63

1-(3,4-Dihydroxy-6-nitrobenzyl)-4-cyclohexylcarbonyl piperidine 0.48 g of the above product was treated with methanesulfonic acid in formic acid as described in Example 50. Yield 0.3 g (75%), m.p. 240° C.

EXAMPLE 64

1-(3,4-Cyclohexylidenedioxy-6-nitrobenzoyl)-4-(1-piperidyl)piperidine

The procedure described in Example 62 was repeated using 0.3 g of 4-(1-piperidyl)piperidine instead of 4-cyclohexylcarbonylpiperidine. Yield 0.57 g (74%), m.p. 200° C.

EXAMPLE 65

Cyclohexyl-4-[1-(3,4-cyclohexylidenedioxy-6-nitrobenzoyl)piperidyl]carbinol

To a solution containing 0.5 g of the product obtained in Example 62 and 1.1 ml of 1N NaOH in 20 ml of methanol 0.1 g of sodium borohydride was added at room temperature. The solution was acidified with acetic acid and extracted with dichloromethane. The solvent was removed in reduced pressure and the residue treated with petroleum ether. Yield 0.45 g (90%), m.p. 155° C.

EXAMPLE 66

1-(3,4-Dihydroxy-6-nitrobenzoyl)-4-(1-piperidyl)piperidine hydromesylate 0.3 g of the product obtained in Example 64 was treated with methanesulfonic acid in formic acid as described in Example 50. Yield 0.26 g (84%), m.p. 290° C.

EXAMPLE 67

1-(3,4-Diacetoxy-6-nitrobenzoyl)-4-cyclohexylcarbonylpiperidine 0.5 g of the product obtained in Example 63 was heated in 10 ml of acetic anhydride for 1 h at 40° C. Ice-water was added and the product was filtered. Yield 0.5 g (87%), m.p. 160°–165° C.

EXAMPLE 68

N-Methyl-N-propargyl-3,4-cyclohexylidenedioxy-6-nitrobenzamide 0.5 g of 3,4-cyclohexylidenedioxy-6-nitrobenzoic acid was converted to the corresponding acid chloride and added to a solution containing 0.12 g methylpropargylamine and 0.18 g of triethylamine in 20 ml of dichloromethane. Yield 0.3 g (50%), m.p. 50°–55° C.

EXAMPLE 69

1-(3,4-Dimethoxy-6-nibrobenzoyl)-4-cyclohexylcarbonyl piperidine 10.3 g of 3,4-dimethoxy-6-nitrobenzoic acid was converted to the corresponding acid chloride as described in Example 43. It was added to a solution containing 8.83 g of 4-cyclohexylcarbonylpiperidine and 4.58 g of triethylamine in 300 ml of dichloromethane. Yield 16.4 g (90%), m.p. 120°–125° C.

EXAMPLE 70

1-(3,4-Dihydroxy-6-nitrobenzoyl)-4-cyclohexylcarbonylpiperidine

A solution containing 0.81 g of the above compound in 12 ml of 1 molar $BBr_3-CH_2Cl_2$ was stirred over night at 20° C. Water was added and the product was filtered. Yield 0.5 g (67%), m.p. 240° C.

EXAMPLE 71

Cyclohexyl-4-[1-(3,4-dimethoxy-6-nitrobenzoyl)piperidyl]carbinol 2.03 g of the product obtained in Example 69 was reduced with sodium borohydride as described in Example 65. Yield 1.89 g (93%), m.p. 145°–150° C.

EXAMPLE 72

3-(3-Ethoxycarbonylmethylcarbamoyloxy-4-hydroxy-5-nitrophenyl)-1-phenylprop-2-en-1-one 1.5 g of ethyl isocyanatoacetate was added to a solution containing 0.54 g of the product obtained in Example 8 in 10 ml of tetrahydrofuran and the solution was stirred for 3 days at 20° C. The solvent was evaporated in reduced pressure and the raw product was purified in a silica gel column using toluene-dioxane-acetic acid (8:1:1) as an eluent. Crystallization from acetone-petroleum ether yielded 0.13 g (17%) of the desired product desired, m.p. 155°–158° C.

EXAMPLE 73

3-(3,4-Methylenedioxy-6-nitrophenyl)-1-phenylprop-2-en-1-one

The procedure described in Example 8 was repeated by using 1.95 g of 6-nitropiperonal and 2.10 g of 3',4',5'-trimethoxyacetophenone in 30 ml of methanol. Yield 0.88 (24%), m.p. 157°–159° C.

EXAMPLE 74

3-(4-Hydroxy-3-methoxy-5-nitrophenyl)-1-(3,4,5-trimethoxyphenyl)prop-2-en-1-one

The procedure described in Example 8 was repeated by using 2.0 g of 4-hydroxy-3-methoxy-5-nitrobenzaldehyde and 2.1 g of 3',4',5'-trimethoxyacetophenone. Yield 2.2 g (57%), m.p. 123°–125° C.

EXAMPLE 75

3-(3,4-Dihydroxy-5-nitrophenyl)-1-(2-carboxyphenyl)-prop-2-en-1-one

The procedure described in Example 8 was repeated using 1.83 g of 3,4-dihydroxy-5-nitrobenzaldehyde and 1.64 g of 2'-carboxyacetophenone. Yield 0.36 g (11%), m.p. 178°–180° C.

EXAMPLE 76

3-(3,4-Dihydroxy-5-nitrophenyl)-1-(4-nitrophenyl)-prop-2-en-1-one

The procedure described in Example 8 was repeated using 1.83 g of 3,4-dihydroxy-5-nitrobenzaldehyde and 1.65 g of 4'-nitroacetophenone. Yield 1.25 g (38%), m.p. 255°–256° C.

EXAMPLE 77

3-(3-methoxy-4-hydroxy-5-trifluoromethylphenyl)-1-(3,4,5-trimethoxyphenyl)prop-2-en-1-one The procedure described in Example 8 was repeated using 2.2 g of 3-methoxy-4-hydroxy-5-trifluoromethylbenzaldehyde and 2.1 g of 3',4',5'-trimethoxyacetophenone. Yield 2.6 g (61%), m.p. 190°–192° C.

EXAMPLE 78

4-(3,4-Dimethoxy-5-methylsulfonylphenyl)-3-methylbut-3-en-2-one

The procedure described in Example 8 was repeated using 2.44 g of 3,4-dimethoxy-5-methylsulfonylbenzaldehyde and 1.0 g of 2-butanone. Yield 2.0 g (63%), viscous oil.

EXAMPLE 79

2,5-Bis-(3,4-dihydroxy-5-nitrobenzylidene)cyclopentanone

The procedure described in Example 8 was repeated using 5.0 g of 3,4-dihydroxy-5-nitrobenzaldehyde and 2.0 g of cyclopentanone. Yield 4.4 g (78%), m.p. 300° C. (decomp.).

EXAMPLE 80

1-Phenyl-3-(3-stearoyloxy-4-hydroxy-5-nitrophenyl)-prop-2-en-1-one

A solution containing 2.0 g of the product obtained in Example 8 and 10.0 g of stearoyl chloride in 10 ml of dioxane was stirred and heated for 18 h at 90° C. After cooling petroleum ether was added and the product was filtered. Recrystallization from dichloromethane-petroleum ether yielded 0.64 g (17%) of the desired product desired, m.p. 112°–118° C.

EXAMPLE 81

Ethyl 2-cyano-3-(3,4-dihydroxy-5-nitrophenyl)acrylate

The procedure described in Example 4 was repeated using 1.0 g of 3,4-dihydroxy-5-nitrobenzaldehyde, 0.9 g of ethyl cyanoacetate and 0.15 g of ammonium acetate in 10 ml of ethanol. Yield 0.87 g (57%), m.p. 205°–210° C.

EXAMPLE 82

Methyl 3-(3,4-dihydroxy-5-nitrobenzylidine)-4-ketopentanoate

A solution containing 1.83 g of 3,4-dihydroxy-5-nitrobenzaldehyde and 1.1 g of levulinic acid in 10 ml of methanol was saturated with gaseous hydrogen chloride. The mixture was refluxed for 20 h after which water was added and the solution was extracted with ether. The solvent was evaporated in reduced pressure and the residue crystallized from ether-petroleum ether. Yield 0.54 g (20%), m.p. 142°–150° C.

EXAMPLE 83

3,4-Dihydroxy-5-nitrobenzylmalonitrile 1.5 g of sodium borohydride was added to a suspension containing 3.7 g of the product obtained in Example 5 in 10 ml of water at room temperature. The solution was stirred for 2 h more, acidified with hydrochloric acid and extracted with ether. The solvent was evaporated in vacuo and the residue crystallized from methanol-isopropanol. Yield 1.1 g (30%), m.p. 211°–215° C.

EXAMPLE 84

Ethyl 3,4-dihydroxy-5-nitrobenzylcyanoacetate

The procedure described in Example 83 was repeated using 2.78 g of the product obtained in Example 81. Yield 0.98 g (35%), yellow viscous oil.

EXAMPLE 85

1-Phenyl-3-(3-methoxy-4-hydroxy-5-trifluoromethylphenyl)prop-2-en-1-one

The procedure described in Example 8 was repeated using 1.7 g of 3-methoxy-4-hydroxy-5-trifluoromethylbenzaldehyde and 1.0 g of acetophenone. Yield 1.1 g (45%), m.p. 166°–168° C.

EXAMPLE 86

1-Phenyl-3-(3,4-dihydroxy-5-trifluoromethylphenyl)-prop-2-en-1-one

To a solution containing 0.32 g of the above product obtained in Example 85 in 10 ml of dichloromethane 3 ml of 1 molar $BBr_3$-$CH_2Cl_2$ was added. The mixture was stirred for 20 min at room temperature, acidified with 10 ml 2 N hydrochloric acid and extracted with dichloromethane. The solvent was evaporated in reduced pressure and the residue crystallized from acetone-dichloromethane. Yield 0.07 g (23%), m.p. 196°–201° C.

EXAMPLE 87

3,4-Dihydroxy-5-sulfonamidobenzaldehyde

A solution containing 1.89 g of 2,3-dihydroxybenzenesulfonamide and 1.4 g of hexamethylenetetramine in 20 ml of trifluoroacetic acid was refluxed for 2 h. The solvent was evaporated in vacuo, water was added to the residue and the product was filtered. Yield 0.78 g (35%).

EXAMPLE 88

2-Methoxy-6-trifluoromethylphenol

A solution containing 160 ml of 1.6 molar butyllithium in hexane, 300 ml of tetrahydrofuran and 40 ml of N,N,N',N'-tetramethylethylenediamine was cooled to −78° C. and 43.3 g of 3-trifluoromethylanisole was added with stirring under nitrogen atmosphere. The solution was allowed to warm up to room temperature and cooled then again to −78° C. after which 35 ml of trimethyl borate was added. The solution was warmed up to 20° C. and 50 ml of conc. ammonia solution was added. The solvents were evaporated in reduced pressure and to the residue 60 ml of 98–100% formic acid followed with 25 ml of 35% hydrogen peroxide were added. The solution was extracted with ether-petroleum ether (1:1). The organic phase was separated and the product was extracted with 2.5 N NaOH-solution. The aqueous phase was acidified with hydrochloric acid and the product was extracted in dichloromethane. The solvent was removed for the most part in vacuo after which petroleum ether was added. The crystalline product was filtered, yield 8.5 g (18%), m.p. 51°–53° C.

EXAMPLE 89

4-Hydroxy-3-methoxy-5-trifluoromethylbenzaldehyde

A solution containing 1.9 g of 2-methoxy-6-trifluoromethylphenol and 1.4 g of hexamethylenetetramine in 20 ml of trifluoroacetic acid was refluxed for 1 h. The solvent was removed in reduced pressure, 50 ml of 1 N hydrochloric acid was added to the residue and the solution was extracted with dichloromethane. Most part of the solvent was evaporated in vacuo and petroleum ether was added, whereupon the product crystallized. Yield 0.7 g (32%), m.p. 151°–152° C.

EXAMPLE 90

3,4-Dimethoxy-5-cyanobenzaldehyde

A mixture containing 2.5 g of 3,4-dimethoxy-5-bromobenzaldehyde and 1.0 g of cuprous cyanide in N-methylpyrrolidone was refluxed for 2 h. Water was added and the solution was extracted with dichloromethane. The solvent was evaporated in vacuo. Yield 1.55 g (81%), m.p. 109°–112° C.

EXAMPLE 91

3,4-Dihydroxy-5-cyanobenzaldehyde

A solution containing 0.96 g of the above product in 15 ml of 1 molar $BBr_3$-$CH_2Cl_2$-solution was stirred for 4 h at room temperature under nitrogen. 15 ml of 1 N hydrochloric acid was added and the dichloromethane phase was separated. The solvent was evaporated in vacuo. Yield 0.61 g (75%), m.p. 210°–215° C.

EXAMPLE 92

1,2-Dimethoxy-3-methylsulfonylbenzene

To a solution containing 3.68 g of 2,3-dimethoxythioanisole in 50 ml of dichloromethane 3.6 g of 3-chloroperoxybenzoic acid was added with stirring. Stirring was continued for 18 h more at room temperature. 30 ml of 1 N NaOH-solution was added, dichloromethane phase was separated and the solvent evaporated in vacuo. Yield 4.51 g (91%), a viscous oil.

EXAMPLE 93

3,4-Dimethoxy-5-methylsulfonylbenzaldehyde

The procedure described in Example 80 was repeated using 2.16 g of 2,3-dimethoxy-3-methylsulfonylbenzene and 1.4 g of hexamethylenetetramine. Yield 0.97 g (45%), a viscous oil.

EXAMPLE 94

3,4-Dihydroxy-5-methylsulfonylbenzaldehyde

A solution containing 0.5 g of the above product and 5 ml of 48% hydrobromic acid in 5 ml of acetic acid was refluxed for 8 h. Water was added and the solution was extracted with dichloromethane. The solvent was evaporated in vacuo. Yield 0.3 g (68%), a viscous oil.

EXAMPLE 95

3,4-Dihydroxy-5-cyanobenzaldehyde

A solution containing 1.35 g of 2,3-dihydroxybenzonitrile and 1.4 g of hexamethylene tetramine in 20 ml of trifluoroacetic acid was refluxed for 1.5 h. Water was added and the product was filtered. Yield 0.9 g (55%), m.p. 211°–215° C.

EXAMPLE 96

3-(3,4-Dihydroxy-5-trifluoromethylphenyl)-1-phenyl-prop-2-en-1-one

The procedure described in Example 8 was repeated using 2.06 g of 3,4-dihydroxy-5-trifluoromethylbenzaldehyde and 1.20 g of acetophenone. Yield 2.19 g (71%), m.p. 196°–210° C.

EXAMPLE 97

3,4-Dihydroxy-5-trifluoromethylbenzaldehyde

A solution containing 2.2 g of 4-hydroxy-3-methoxy-5-trifluoromethylbenzaldehyde in 65 ml of 1 molar $BBr_3$ in dichloromethane was stirred for 2 h at room temperature. Hydrochloric acid was added and the organic phase was separated. The solvent was evaporated in vacuo. Yield 1.4 g (68%), m.p. 188°–192° C.

EXAMPLE 98

2-Cyano-3-(3,4-dihydroxy-5-nitrophenyl)acrylamide

A solution containing 1.3 g of 3,4-dihydroxy-5-nitrobenzaldehyde, 0.73 g of cyanoacetamide and catalytic amount of piperidine acetate in 40 ml of dry ethanol was refluxed over night. The solvent was evaporated in vacuo and the residue was recrystallized water-DMF. Yield 0.84 g (48%), m.p. 296°–298° C.

EXAMPLE 99

N,N-Dimethyl-2-cyano-3-(3,4-dihydroxy-5-nitrophenyl)acrylamide

A solution containing 1.83 g of 3,4-dihydroxy-5-nitrobenzaldehyde, 1.2 g of N,N-dimethylcyanoacetamide and catalytic amount of piperidine acetate in 40 ml of dry ethanol was refluxed over night. Yield 1.1 g (40%), m.p. 183°–185° C.

EXAMPLE 100

N,N-Diethyl-2-cyano-3-(3,4-dihydroxy-5-nitrophenyl)-acrylamide

The procedure described in Example 99 was repeated using 1.83 g of 3,4-dihydroxy-5-nitrobenzaldehyde and 1.5 g of N,N-Hydrochloric diethylcyanoacetamide. Yield 2.23 g (73%), m.p. 153°–156° C.

EXAMPLE 101

N-Isopropyl-2-cyano-3-(3,4-dihydroxy-5-nitrophenyl)acrylamide

The procedure described in Example 99 was repeated using 1.83 g of 3,4-dihydroxy-5-nitrobenzaldehyde and 1.3 g of N-isopropylcyanoacetamide. Yield 1.46 g (50%), m.p. 243°–245° C.

EXAMPLE 102

N'-Methyl-N''-/2-cyano-3-(3,4-dihydroxy-5-nitrophenyl)-acryl/piperazine

The procedure described in Example 99 was repeated using 1.83 g of 3,4-dihydroxy-5-nitrobenzaldehyde and 1.7 g of N'-methyl-N''-cyanoacetylpiperazine. Yield 2.16 g (65%), m.p. 265° C. (decomp.).

EXAMPLE 103

3-(3,4-Dihydroxy-5-trifluoromethylbenzylidene)-2,4-pentanedione

The procedure described in Example 7 was repeated using 2.06 g of 3,4-dihydroxy-5-trifluoromethyl-benzaldehyde and 1.00 g of 2,4-pentanedione. Yield 1.39 g (45%), m.p. 198°–205° C.

EXAMPLE 104

3,4-Dihydroxy-5-nitrobenzylalcohol

To a solution containing 6.0 g of sodium borohydride in 50 ml of water 9.15 g of 3,4-dihydroxy-5-nitrobenzaldehyde was gradually added with stirring at room temperature. The mixture was stirred for 1 h more after which it was acidified with hydrochloric acid. The solution was filtered to remove tarry impurities and extracted 4 times with ether. The ether extract was dried over anhydrous sodium sulfate, filtered and concentrated to a volume of about 100 ml.

The crystalline solid was filtered. Yield 6.0 g (65%), m.p. 100° C. (decomp.).

EXAMPLE 105

3,4-Dihydroxy-5-nitrobenzyl-2-methoxyethylether

A solution of 1.0 g of 3,4-dihydroxy-5-nitrobenzylalcohol in 5.0 ml of 2-methoxyethanol was refluxed for 1 h. The solvent was evaporated in vacuo and the residue was triturated with isopropanol. Yield 0.4 g (30%), m.p. 154°–157° C.

EXAMPLE 106

3,4-Dihydroxy-5-nitrobenzylthioacetic acid

A solution containing 1.0 g of 3,4-dihydroxy-5-nitrobenzylalcohol in 5.0 g of thioglycolic acid was stirred for 1.5 h at 120° C. 25 ml of water was added and product was filtered and washed with water. Yield 0.25 g (19%), m.p. 91°–93° C.

EXAMPLE 107

2-(3,4-Dihydroxy-5-nitrobenzyl)pyrrole

A solution containing 1.0 g of 3,4-dihydroxy-5-nitrobenzylalcohol and 5.0 ml of pyrrole in 3.0 ml of dioxane was heated for 5 h at 100° C. Water was added and the solution was extracted with dichloromethane. The solvent was evaporated and the residue was purified in a silicagel column using toluene-acetic acid-dioxane (18:1:1) mixture as an eluent. Yield 0.42 g (33%), m.p. 115°–118° C.

EXAMPLE 108

2-Cyano-3-(3,4-dihydroxy-5-nitrophenyl)propanol

To a solution containing 0.85 g of ethyl 2-cyano-3-(3,4-dihydroxy-5-nitrophenyl)acrylate (Example 81) in 70 ml of dry ethanol 0.3 g of sodium borohydride was gradually added. The solution was stirred for 0.5 h at room temperature, acidified with hydrochloric acid and extracted with ethyl acetate. The solvent was evaporated yielding 0.55 g (75%) of yellow crystals, m.p. 149°–152° C.

EXAMPLE 109

3-Nitrocatechol

To a solution containing 2.5 g of catechol in 125 ml of ether 1.0 ml of conc. nitric acid (d=1.52) was gradually added. The solution was stirred over night at room temperature and washed with water. The solvent was evaporated and the residue was treated with boiling petroleum ether (b.p. 60°–80° C.). The insoluble 4-nitrocatechol was filtered and the filtrate concentrated in vacuo. After cooling the 3-nitrocatechol was filtered. Yield 0.85 g (24%), m.p. 82°–85° C.

EXAMPLE 110

3,5-Dinitrocatechol

To a solution containing 50.0 g of catechol diacetate in 250 ml of acetic acid 125 ml of nitric acid (d=1.42) was gradually added at 50° C. The solution was stirred for 1.5 h more at 50° C. and poured then to crushed ice. The product was filtered, washed with water and dissolved in 500 ml of methanol containing 1.0 ml of conc. sulfuric acid. The solution was refluxed for 2.5 h. Methanol was distilled off to a great extend and 100 ml of water was added. The remaining methanol was evaporated in vacuo whereupon the product was crystallized. Yield 20.9 g (40.4%), m.p. 168°–170° C.

EXAMPLE 111

3,4-Dihydroxy-5-nitrobenzaldehyde

A solution containing 8.0 kg of 5-nitrovanillin and 8.7 kg of acetic acid in 35 kg of conc. hydrobromic acid was refluxed for 20 h. 0.6 kg of charcoal was added and the mixture was filtered. 32 kg of water was added with stirring and the solution was cooled to −10° C. and stirring was continued for 2 h more. The crystalline product was filtered and washed with water. Yield 5.66 kg (80%), m.p. 135°–137° C.

EXAMPLE 112

3,4-Dihydroxy-5-nitrobenzonitrile

A solution containing 0.92 g of 3,4-dihydroxy-5-nitrobenzaldehyde and 0.49 g of hydroxylamine hydrochloride in 5.0 ml of formic acid was refluxed for 1 h. 50 ml of water was added and the product was filtered and washed with water. Yield 0.3 g (33%), m.p. 175°–178° C.

EXAMPLE 113

4-Chloro-6-nitrocatechol

A mixture containing 1.0 g of 4-chloro-3-methoxy-6-nitrophenol in 20 ml of conc. hydrobromic acid was refluxed for 2 h. After cooling the product was filtered and washed with water. Yield 0.6 g (65%), m.p. 108°–111° C.

EXAMPLE 114

4,5-Dihydroxyisophtalaldehyde

To a suspension containing 1.8 g of 4-hydroxy-5-methoxyisophtalaldehyde in 20 ml of dichloromethane was added 35 ml of 1 molar $PBr_3$ in dichloromethane. The mixture was allowed to stand over night at room temperature and poured the to ice-water. Dichloromethane was evaporated in vacuo. After cooling the product was filtered and washed with water. Yield 0.94 g (57%), m.p. 192°–195° C.

EXAMPLE 115

3,4-Dihydroxy-5-cyanobenzoic acid

To a solution containing 2.3 g of 4-acetoxy-3-cyano-5-methoxybenzoic acid in 10 ml of dichloromethane 40 ml of 1 molar $PBr_3$ in dichloromethane was added. The mixture was stirred over night at room temperature. The solvent was evaporated in vacuo and to the residue ice-water was added.

The product was filtered and washed with water. Yield 1.25 g (74%), m.p. 269°–271° C.

EXAMPLE 116

3,4-Dihydroxy-5-nitrophenylalanine hydrobromide

A solution containing 1.2 g of 4-hydroxy-3-methoxy-5-nitrophenylalanine hydrosulfate in 10 ml of conc. hydrobromic acid was refluxed for 2 h. The solution was concentrated in vacuo and allowed to stand over night in a refrigerator. The product was filtered and washed with hydrobromic acid and dried. Yield 0.25 g, m.p. 170° C. (decomp.).

EXAMPLE 117

3,5-Dicyanocatechol

A solution containing 0.83 g of 3,5-diformylcatechol and 0.90 g of hydroxylamine hydrochloride in 30 ml of formic acid was refluxed for 16 hours. Formic acid was evaporated in vacuo and water was added to the residue. The solution was extracted with ether. The solvent was evaporated and the residue was crystallized from ethanol-water. Yield 0.28 g (43%), m.p. 300° C. (decomp.).

EXAMPLE 118

N,N-diethyl-5-chloro-2,3-dihydroxybenzenesulfonamide

To a solution containing 0.7 g of N,N-diethyl-5-chloro-3,4-dimethoxybenzenesulfonamide in 10 ml of dichloromethane 9.0 ml of 1 molar $BBr_3$ in dichloromethane was added. The solution was stirred overnight at room temperature. Water and hydrochloric acid were added and the mixture was extracted with dichloromethane. The solvent was evaporated. Yield 0.3 g (47%), m.p. 62°–64° C.

EXAMPLE 119

4-Chloro-6-methylsulfonylcatechol

The procedure described in Example 118 was repeated using 4-chloro-2-methoxy-6-methylsulfonylphenol. Yield 50%, m.p. 142°–145° C.

EXAMPLE 120

4-Nitro-6-methylsulfonylcatechol

The procedure described in Example 118 was repeated using 2-methoxy-4-nitro-6-methylsulfonylphenol. Yield 21%, m.p. 221°–224° C.

EXAMPLE 121

3,4-Dihydroxy-5-methylsulfonylbenzaldehyde

The procedure described in Example 118 was repeated using 4-hydroxy-3-methoxy-5-methylsulfonylbenzaldehyde. Yield 17%, m.p. 169°–171° C.

EXAMPLE 122

N-(3-hydroxypropyl)-3,4-dihydroxy-5-nitrobenzamide

The procedures described in Examples 43 and 44 were repeated using 3,4-diacetoxy-5-nitrobenzoic acid and 3-aminopropan-1-ol. Yield 85%, m.p. 160°–163° C.

EXAMPLE 123

Neopentyl 2-cyano-3-(3,4-dihydroxy-5-nitrophenyl)acrylate

The procedure described in Example 4 was repeated using 3,4-dihydroxy-5-nitrobenzaldehyde and neopentyl cyanoacetate. Yield 67%, m.p. 173°–179° C.

EXAMPLE 124

N-(3-hydroxypropyl)-2-cyano-3-(3,4-dihydroxy-5-nitrophenyl)acrylamide.

The procedure described in Example 99 was repeated using N-(3-hydroxypropyl)cyanoacetamide and 3,4-dihydroxy-5-nitrobenzaldehyde. Yield 52%, m.p. 223°–228° C.

EXAMPLE 125

2,3-Dihydroxy-5-nitrobenzonitrile

The procedure described in Example 118 was repeated using 2-hydroxy-3-methoxy-5-nitrobenzonitrile. Yield 45%.

EXAMPLE 126

3,5-Dicyanocatechol

To a solution containing 2,4-dicyano-6-methoxyphenol in 20 ml of dichloromethane 20 ml of 1 molar solution of $BBr_3$ in dichloromethane was added. The solution was stirred overnight at room temperature. Water and hydrochloric acid were added and the mixture was extracted with dichloromethane. The solvent was evaporated. Yield 0.8 g (50%), m.p. 300° C. (decomp.).

EXAMPLE 127

1,2-Diacetoxy-3,5-dinitrobenzene

A catalytic amount of concentrated sulfuric acid was added to a solution containing 2.0 g of 3,5-dinitrocatechol in 15 ml of acetanhydride and the solution was mixed for ½ hours in 50°–60° C. Ice water was added to the reaction mixture and the solution was mixed in 0° C. whereby the product was crystallized. The product was filtered and washed with water and dried. Yield 2.75 g (97%), m.p. 115°–117° C.

EXAMPLE 128

1,2-Dipropionyloxy-3,5-dinitrobenzene

The procedure of Example 127 was repeated using propionic acid anhydride instead of acetanhydride. Yield 2.8 g (90%), m.p. 72°–73° C.

EXAMPLE 129

1,2-Dibutyryloxy-3,5-dinitrobenzene

The procedure described in Example 127 was repeated using butyrylanhydride instead of acetanhydride. Yield 70%, m.p. 55°–60°.

EXAMPLE 130

2-Butyryloxy-4,6-dinitrophenol 8.7 ml of nitric acid (d=1.42) was added stirring and cooling to a solution containing 2.4 g of catechol dibutyrate in 25 ml of acetic acid. The solution was stirred for further ½ hours and ice water was added thereto. The product was filtered and washed with water. Yield 1.85 g (53%), m.p. 65°–70° C.

EXAMPLE 131

2-Pivaloyloxy-4,6-dinitrophenol 6.7 ml of nitric acid (d=1.42) was added stirring and cooling (in 20°–25° C.) to a solution containing 1.94 g of catechol monopivaloate in 20 ml of acetic acid. The solution was stirred for ½ hours in 50° C. Ice water was added and the product was filtered and washed with water. Yield 1.75 g (62.5%). m.p. 132°–135° C.

EXAMPLE 132

2-Benzoyloxy-4,6-dinitrophenol

A mixture containing 2.0 g of 3,5-dinitrocatechol in 5 ml of benzoylchloride was cooked for 4 hours in 100° C. When cooled petroleum ether (b.p. 40° C.) was added and the product was filtered and washed with petroleum ether. The raw product was crystallized from ethanol. Yield 2.5 g (82%), m.p. 150°–152° C.

EXAMPLE 133

3-(4-Hydroxy-5-nitro-3-pivaloyloxybenzylidene)-2,4-pentanedione

A mixture containing 2.0 g of the product obtained according to Example 7 in 5 ml of pivaloylchloride was heated for 4 hours in 100° C. The excess pivaloylchloride was evaporated away in reduced pressure and ether was added to the residue. The product was filtered and washed with ether. Yield 1.41 g (58%), m.p. 143°–145° C.

EXAMPLE 134

2-(2,6-Dimethylbenzoyloxy)-4,6-dinitrophenol

A mixture containing 2.0 g of 3,5-dinitrocatechol in 5 ml of 2,6-dimethylbenzoylchloride was heated for 20 hours in 100° C. The excess 2,6-dimethylbenzoylchloride was removed in high vacuum. The residue was purified in silicagel column. Yield 1.5 g (45%), yellow viscous oil, which was crystallized from petroleum ether, m.p. 163°–165° C.

EXAMPLE 135

2-(2,6-dimethoxybenzoyloxy)-4,6-dinitrophenol

The procedure of Example 134 was repeated using 2,6-dimethoxybenzoylchloride. Yield 1.3 g (36%), m.p. 217°–218° C.

EXAMPLE 136

2-(1-Methylcyclohexylcarbonyloxy)-4,6-dinitrophenol

The procedure of Example 134 was repeated using 1-methylcyclohexylcarboxylic acid chloride. Yield 1.6 g (49%), yellow viscous oil.

EXAMPLE 137

1,2-Bis(2,6-dimethylbenzoyloxy)-3,5-dinitrobenzene

The procedure of Example 134 was repeated using a temperature of 134° C. The product was crystallized from 50% ethanol. M.p. 175°–178° C. Yield 60%.

EXAMPLE 138

1,2-Bis(3-ethoxycarbonylpropionyloxy)-3,5-dinitrobenzene

A solution containing 1 g of 3,5-dinitrocathecol in 2,5 ml of ethyl ester chloride of succinic acid was heated for 3 h in 100° C. The product was purified in silicagel column. M.p. 60°–63° C.

What is claimed is:

1. A pharmaceutical composition for inhibiting catechol-O-methyl-transferase, said composition comprising a catechol-O-methyl-transferase inhibiting amount of a compound having the formula I

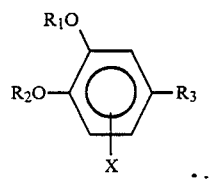

wherein $R_1$ and $R_2$ independently represent hydrogen or alkylcarbonyl of 2 to 5 carbon atoms, X represents nitro or cyano and $R_3$ represents

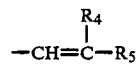

wherein $R_4$ represents cyano or alkylcarbonyl of 2 to 5 carbon atoms and $R_5$ represents cyano; alkylcarbonyl of 2 to 5 carbon atoms; alkoxycarbonyl of 2 to 9 carbon atoms; or carbamoyl which is unsubstituted or substituted with alkyl of 1 to 8 carbon atoms, or hydroxyalkyl of 1 to 8 carbon atoms, and a pharmaceutically acceptable carrier.

2. The pharmaceutical composition as claimed in claim 1, wherein X is nitro.

3. The pharmaceutical composition as claimed in claim 1, wherein $R_4$ and $R_5$ are both alkylcarbonyl of 2 to 3 carbon atoms.

4. A pharmaceutical composition for inhibiting catechol-O-methyl-transferase, said composition comprising a catechol-O-methyl-transferase inhibiting amount of 3-(3,4-dihydroxy-5-nitrobenzylidene)-2,4-pentanedione, and a pharmaceutically acceptable carrier.

5. A pharmaceutical composition as claimed in claim 1, wherein R4 represents cyano and R5 represents carbamoyl which is unsubstituted or substituted with alkyl of 1 to 8 carbon atoms or hydroxyalkyl of 1 to 8 carbon atoms.

6. The pharmaceutical composition as claimed in claim 5, wherein R5 represents carbamoyl which is substituted with methyl, ethyl, isopropyl or hydroxypropyl.

7. A pharmaceutical composition for inhibiting catechol-O-methyl-transferase, said composition comprising a catechol-O-methyl-transferase inhibiting amount of N,N-diethyl-2-cyano-3-(3,4-dihydroxy-5-nitrophenyl)acrylamide, and a pharmaceutically acceptable carrier.

8. A method for inhibiting catechol-O-methyl-transferase in a patient, said method comprising administering a catechol-O-methyl-transferase inhibiting amount of a compound having the formula I

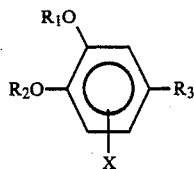

wherein $R_1$ and $R_2$ independently represent hydrogen or alkylcarbonyl of 2 to 5 carbon atoms, X represents nitro or cyano and $R_3$ represents

wherein R4 represents cyano or alkylcarbonyl of 2 to 5 carbon atoms and R5 represents cyano; alkylcarbonyl of 2 to 5 carbon atoms; alkoxycarbonyl of 2 to 9 carbon atoms; or carbamoyl which is unsubstituted or substituted with alkyl of 1 to 8 carbon atoms, or hydroxyalkyl of 1 to 8 carbon atoms, to a patient in need of such treatment.

9. The method as claimed in claim 8, wherein X is nitro.

10. The method as claimed in claim 8, wherein R4 and R5 are both alkylcarbonyl of 2 to 3 carbon atoms.

11. A method for inhibiting catechol-O-methyl-transferase in a patient, said method comprising administering a catechol-O-methyl-transferase inhibiting amount of 3-(3,4-dihydroxy-5-nitrobenzylidene)-2,4-pentanedione, to a patient in need of such treatment.

12. A method as claimed in claim 8, wherein R4 represents cyano and R5 represents carbamoyl which is unsubstituted or substituted with alkyl of 1 to 8 carbon atoms or hydroxyalkyl of 1 to 8 carbon atoms.

13. The method as claimed in claim 12, wherein R5 represents carbamoyl which is substituted with methyl, ethyl, isopropyl or hydroxypropyl.

14. A method for inhibiting catechol-O-methyl-transferase in a patient, said method comprising administering a catechol-O-methyl-transferase inhibiting amount of N,N-diethyl-2-cyano-3-(3,4-dihydroxy-5-nitrophenyl)acrylamide, to a patient in need of such treatment.

* * * * *

UNITED STATES PATENT AND TRADEMARK OFFICE
CERTIFICATE OF CORRECTION

PATENT NO. : 4,963,590

DATED : October 16, 1990

INVENTOR(S) : Reijo Bäckström et al.

It is certified that error appears in the above-identified patent and that said Letters Patent is hereby corrected as shown below:

ON TITLE PAGE: Item [30] should read

[30] Foreign Application Priority Data

Nov. 28, 1986 [FI] ..........864875

May 27, 1987 [GB] ...........87 12437

Signed and Sealed this

Twelfth Day of May, 1992

*Attest:*

DOUGLAS B. COMER

*Attesting Officer*     *Acting Commissioner of Patents and Trademarks*